(12) United States Patent
Kim

(10) Patent No.: US 10,241,042 B2
(45) Date of Patent: Mar. 26, 2019

(54) WEARABLE DEVICE AND CHARGER, AND METHOD FOR ESTIMATING ABSORBANCE OF WEARABLE DEVICE

(71) Applicant: SAMSUNG ELECTRONICS CO., LTD., Suwon-si (KR)

(72) Inventor: Sang Kyu Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 7 days.

(21) Appl. No.: 15/390,003

(22) Filed: Dec. 23, 2016

(65) Prior Publication Data

US 2018/0024056 A1    Jan. 25, 2018

(30) Foreign Application Priority Data

Jul. 21, 2016  (KR) .................... 10-2016-0092793

(51) Int. Cl.
| | | |
|---|---|---|
| *G01J 3/28* | (2006.01) | |
| *G01N 21/49* | (2006.01) | |
| *G01N 21/47* | (2006.01) | |
| *G04G 21/02* | (2010.01) | |
| *A61B 5/00* | (2006.01) | |

(52) U.S. Cl.
CPC ........... *G01N 21/49* (2013.01); *A61B 5/0075* (2013.01); *A61B 5/681* (2013.01); *G01N 21/4785* (2013.01); *G04G 21/02* (2013.01); *A61B 2560/0214* (2013.01)

(58) Field of Classification Search
CPC .......... H02H 9/04; H02H 9/046; G04G 21/00; G06F 1/163; G06F 1/263; H01R 13/6485; H02J 7/007; H02J 7/0036; A61B 5/1455; A61B 5/145; A61B 5/14552

USPC ............ 356/432–440, 39–42, 300, 326, 319; 600/310, 322–325, 339, 340; 320/162
See application file for complete search history.

(56) References Cited

U.S. PATENT DOCUMENTS

| | | |
|---|---|---|
| 6,959,211 B2 | 10/2005 | Rule et al. |
| 2006/0183983 A1 | 8/2006 | Acosta et al. |
| 2009/0318802 A1 | 12/2009 | Boyden et al. |

(Continued)

FOREIGN PATENT DOCUMENTS

| | | |
|---|---|---|
| EP | 2510891 A1 | 10/2012 |
| JP | 2007263587 A | 10/2007 |

(Continued)

OTHER PUBLICATIONS

Communication dated Sep. 14, 2017, issued by the European Patent Office in counterpart European Application No. 17156387.7.

(Continued)

*Primary Examiner* — Hoa Q Pham
(74) *Attorney, Agent, or Firm* — Sughrue Mion, PLLC

(57) ABSTRACT

A wearable device, a charger, and a method for estimating absorbance of the wearable device are provided. The wearable device includes a spectroscope configured to emit a first light to a reference material of a charger, measure an intensity of the first light reflected from the reference material, emit a second light to a skin of a user, and measure an intensity of the second light reflected from the skin of the user; and a processor configured to determine absorbance of the skin of the user based on the intensity of the first light and the intensity of the second light.

14 Claims, 9 Drawing Sheets

(56) References Cited

U.S. PATENT DOCUMENTS

| | | | |
|---|---|---|---|
| 2011/0205535 A1* | 8/2011 | Soller | A61B 5/14552 356/300 |
| 2013/0289414 A1 | 10/2013 | Adibnazari et al. | |
| 2014/0246502 A1 | 9/2014 | Proud et al. | |
| 2015/0157261 A1 | 6/2015 | Sakagami | |
| 2015/0241916 A1* | 8/2015 | Choi | G06F 1/163 361/679.03 |
| 2015/0351690 A1 | 12/2015 | Toth et al. | |
| 2016/0028267 A1 | 1/2016 | Lee et al. | |
| 2016/0054423 A1 | 2/2016 | Kang et al. | |
| 2016/0056647 A1 | 2/2016 | Choi | |
| 2016/0058367 A1* | 3/2016 | Raghuram | A61B 5/486 600/479 |
| 2016/0061660 A1 | 3/2016 | Kim | |
| 2016/0073886 A1 | 3/2016 | Connor | |
| 2016/0166150 A1* | 6/2016 | Vilenskii | A61B 5/0077 348/77 |
| 2016/0166153 A1 | 6/2016 | Woo et al. | |
| 2016/0359338 A1* | 12/2016 | Gao | H02J 7/0047 |
| 2017/0040825 A1* | 2/2017 | Cavallaro | H02J 7/025 |
| 2017/0059409 A1* | 3/2017 | Eom | G01J 3/42 |

FOREIGN PATENT DOCUMENTS

| | | |
|---|---|---|
| KR | 101556399 B1 | 10/2015 |
| KR | 1020160011944 A | 2/2016 |
| KR | 1020160024412 A | 3/2016 |
| KR | 1020160024415 A | 3/2016 |

OTHER PUBLICATIONS

Communication dated Jan. 15, 2018, issued by the European Patent Office in counterpart European Application No. 17156387.7.

* cited by examiner

WEARABLE DEVICE AND CHARGER, AND METHOD FOR ESTIMATING ABSORBANCE OF WEARABLE DEVICE

CROSS-REFERENCE TO RELATED APPLICATION

This application claims priority from Korean Patent Application No. 10-2016-0092793, filed on Jul. 21, 2016 in the Korean Intellectual Property Office, the disclosure of which is incorporated herein by reference in its entirety.

BACKGROUND

1. Field

Exemplary embodiments relate to estimating absorbance using a wearable device, and more particularly, to a wearable device and a charger, and a method for estimating absorbance of the wearable device.

2. Description of Related Art

As interest in health increases, various kinds of biometric information detection devices that measure biometric signals in daily life have been developed for user convenience.

Further, the devices are provided in the form of a wearable device which is worn by a person and is capable of directly measuring a biometric state, and are used as a smart healthcare system of providing health-related services in association with a personal health information database and providing a diagnosis/prescription result in association with a remote medical diagnosis to a patient.

Meanwhile, a spectroscope is a device used for detecting light that penetrates or is reflected by a sample, analyzing a structure of the sample, and recognizing a property of the sample.

In order to measure a biometric signal using the spectroscope, it is necessary to measure an intensity of light emitted by the spectroscope for calibration of the spectroscope. In particular, technology capable of conveniently performing the calibration of the spectroscope is needed when the spectroscope is installed in the wearable device.

SUMMARY

One or more exemplary embodiments provide a wearable device, and a method for estimating a light absorbance of a target subject using the wearable device.

According to an aspect of an exemplary embodiment, there is provided a wearable device including: a spectroscope configured to emit a first light to a reference material of a charger, measure an intensity of the first light reflected from the reference material, emit a second light to a skin of a user, and measure an intensity of the second light reflected from the skin of the user; and a processor configured to determine absorbance of the skin of the user based on the intensity of the first light and the intensity of the second light.

The spectroscope may automatically emit the first light to the reference material, and measure the intensity of the first light in response to the wearable device being placed on the charger.

The spectroscope may emit the first light to the reference material at predetermined time intervals, and repeatedly measure the intensity of the first light.

The predetermined time interval may be set by the user, or as default.

The processor may determine a representative intensity representing the intensity of the first light which is repeatedly measured in response to the wearable device being removed from the charger.

The processor may determine at least one of an arithmetic mean value, a weighted mean value, a median value, a mode value, a minimum value, and a maximum value of the intensity of the first light which is repeatedly measured, as the representative intensity.

The processor may determine an intensity of emitting light of the spectroscope by correcting the representative intensity according to a reflectivity of the reference material, and determine the absorbance of the skin of the user using the determined intensity of the emitting light and the intensity of the second light.

When the wearable device is worn by the user, the spectroscope may emit the light to the skin of the user, and measure the intensity of the second light according to an input of the user.

The reference material may include at least one of barium sulfate ($BaSO_4$) and polytetrafluoroethylene (PTEF).

The wearable device may further include a sensor configured to sense whether the wearable device is placed on the charger.

The wearable device may be a wristwatch type or wristband type wearable device.

According to an aspect of another exemplary embodiment, there is provide a charger of a wearable device which includes a spectroscope, the charger including a reference material arranged or coated on a side of the charger facing a light emitting side of the wearable device when the wearable device is installed on the charger.

The reference material may include at least one of barium sulfate ($BaSO_4$) and (polytetrafluoroethylene (PTEF).

According to an aspect of another exemplary embodiment, there is provided a method for operating a wearable device including: emitting a first light to a reference material of a charger; measuring an intensity of the first light reflected from the reference material; emitting a second light to a skin of a user; measuring an intensity of the second reflected from the skin of the user; and determining absorbance of the skin of the user based on the intensity of the first light and the intensity of the second light.

The emitting the first light may include emitting the first light to the reference material of the charge when the wearable device is placed on the charger.

The emitting the first light may include emitting the first light to the reference material at predetermined time intervals, and the measuring the intensity of the first light may include repeatedly measuring the intensity of the first light.

The predetermined time interval may be set by the user, or as default.

The method may further include: determining a representative intensity representing the intensity of the first light which is repeatedly measured in response to the wearable device being removed from the charger; and correcting the representative intensity based on a reflectivity of the reference material, wherein the determining the absorbance of the skin of the user comprises determining the absorbance based on the corrected representative intensity and the intensity of the second light.

The determining the representative intensity may include determining at least one of an arithmetic mean value, a weighted mean value, a median value, a mode value, a minimum value, and a maximum value of the intensity of the first reflective light which is repeatedly measured, as the representative intensity.

The reference material may include at least one of barium sulfate (BaSO$_4$) and polytetrafluoroethylene (PTEF).

The wearable device may be a wristwatch type or wristband type wearable device.

According to an aspect of another exemplary embodiment, there is provided a wearable device including: a storage configured to store a reference reflective intensity; a light emitter configured to emit a light to a user of the wearable device; a spectroscope configured to receive the light reflected from the user and measure an intensity of the light; and a processor configured to determine absorbance of the user based on a comparison between the reference reflective intensity and the intensity of the light measured by the spectroscope.

The light emitter may emit a light to a charger while the wearable device is being charged via the charger, and the spectroscope may receive the light reflected from the charger and measure the reference reflective intensity to be stored in the storage.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
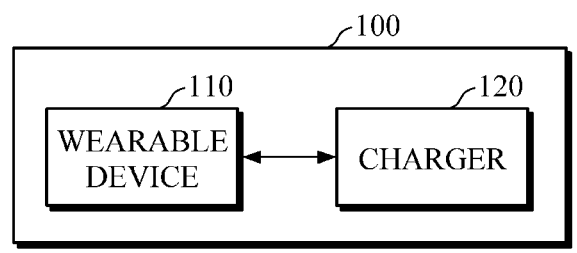
FIG. 1 is a block diagram illustrating a system for estimating absorbance according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Expressions such as "at least one of," when preceding a list of elements, modify the entire list of elements and do not modify the individual elements of the list.

FIG. 1 is a block diagram illustrating a system for estimating absorbance according to an exemplary embodiment.

Referring to FIG. 1, a system for estimating absorbance 100 may include a wearable device 110 and a charger 120.

The wearable device 110 may be a device which is worn by a user and is able to estimate absorbance of a skin of the user, and include wearable devices having various types such as a wristwatch type, a wristband type, a ring type, a belt type, a necklace type, an ankle band type, a thigh band type, a forearm band type, etc. However, they are merely exemplary embodiments, and are not limited thereto.

The wearable device 110 may calculate an intensity of light (hereinafter, emitting light) emitted from the wearable device 110 using a reference material arranged or coated on the charger 120. Here, the reference material may be a diffused reflection material having a reflectivity of 1 to 99%, and include barium sulfate (BaSO$_4$), Teflon (polytetrafluoroethylene (PTEF)), etc.

When the wearable device 110 is plugged into or placed on the charger 120 for charging, the wearable device 110 may automatically emit the light at predetermined time intervals to the reference material which is arranged or coated on the charger 120, receive the light (hereinafter, first reflective light) reflected from the reference material, and repeatedly measure an intensity of the first reflective light. In this case, the predetermined time interval may be set by the user, or as default. The charger 120 may include a wireless charging stand, mat, or pad to provide power to the wearable device 100 wirelessly while the wireless device 100 is placed on the charging stand, mat, or pad. Alternatively, the charger 120 may provide power to the wearable device 100 via wire or cable while the wearable device 100 is plugged into the charge 120.

The wearable device 110 may calculate the intensity of the emitting light based on the intensity of the first reflective light which is repeatedly measured. According to an exemplary embodiment, when the wearable device 110 is removed from the charger 120, the wearable device 110 may calculate a representative intensity representing the intensity of the first reflective light which is repeatedly measured, correct the calculated representative intensity according to the reflectivity of the reference material, and calculate the intensity of the emitting light. In this case, the wearable device 110 may calculate one of the following values, an arithmetic mean value, a weighted mean value, a median value, a mode value, a minimum value, and a maximum value, of the intensity of the first reflective light which is repeatedly measured, as the representative intensity.

When the wearable device 110 is worn by the user, the wearable device 110 may emit the light to the skin of the user according to input of the user, receive the light (hereinafter, second reflective light) reflected from the skin of the user, and measure an intensity of the second reflective light.

The wearable device 110 may calculate absorbance of the skin of the user based on the calculated intensity of the emitting light and the measured intensity of the second reflective light. For example, the wearable device 110 may calculate the absorbance of the skin of the user through the following Equation 1.

$$A = -\log(I_s/I_0) \qquad \text{[Equation 1]}$$

Here, A represents the absorbance, $I_s$ represents the intensity of the second reflective light, and $I_0$ represents the intensity of the emitting light.

The charger 120 may charge a battery of the wearable device 110. Further, when the wearable device 110 is installed for charging, the reference material may be arranged or coated on a side of the charger 120 facing a light emitting side of the wearable device 110. In this case, the reference material may be a diffused reflection material having a reflectivity of 1 to 99%, and include $BaSO_4$, PTEF, etc.

Meanwhile, the charger 120 may include a wired/wireless charger and a stationary/portable charger.

Figure 2:
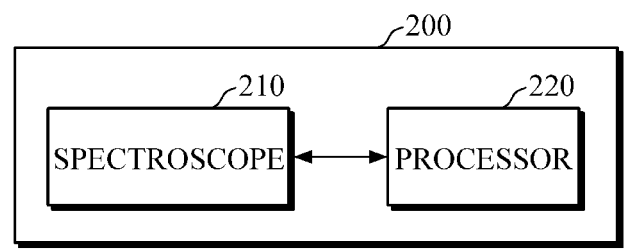
FIG. 2 is a block diagram illustrating a wearable device according to an exemplary embodiment.

FIG. 2 is a block diagram illustrating a wearable device according to an exemplary embodiment. A wearable device 200 shown in FIG. 2 may be an exemplary embodiment of the wearable device 110 shown in FIG. 1.

Referring to FIG. 2, the wearable device 200 may include a spectroscope 210, and a processor 220.

When the wearable device 200 is placed on a charger for charging, the wearable device 200 (e.g., a light emitter disposed in the wearable device 200) may emit light to a reference material. The spectroscope 210 may receive first reflective light reflected from the reference material, and measure an intensity of the first reflective light. In this case, the reference material may be a diffused reflection material having a reflectivity of 1 to 99%, and when the wearable device 200 is installed for charging, may be arranged or coated on a side facing a light emitting side of the wearable device 200. In this case, the reference material may include $BaSO_4$, PTEF, etc. The wearable device 100 may automatically determine whether the wearable device 200 is in contact with the user, and may activate the spectroscope 210 to receive and analyze the light when the wearable device 200 is in contract with the user. For example, when the processor 220 determines that a contract area between a main body of the wearable device 200 and the skin of the user is greater than a threshold value, the spectroscope 210 may measure the intensity of the first reflective light.

According to an exemplary embodiment, when the wearable device 200 is placed on the charger for charging, the spectroscope 210 may automatically emit the light at predetermined time intervals to the reference material which is arranged or coated on the charger, receive the first reflective light reflected from the reference material, and repeatedly measure the intensity of the first reflective light. In this case, the predetermined time interval may be set by the user, or as default.

Further, when the wearable device 200 is removed from the charger and is worn by the user, the spectroscope 210 may emit the light to the skin of the user according to a command of the user, receive second reflective light reflected from the skin of the user, and measure an intensity of the second reflective light.

When the wearable device 200 is removed from the charger, the processor 220 may calculate the intensity of the emitting light of the spectroscope 210 based on the intensity of the first reflective light which is repeatedly measured. For example, the processor 220 may calculate a representative intensity of the intensity of the first reflective light which is repeatedly measured, correct the calculated representative intensity according to a reflectivity of the reference material, and calculate the intensity of the emitting light. In this case, the processor 220 may calculate one of the following values, an arithmetic mean value, a weighted mean value, a median value, a mode value, a minimum value, and a maximum value, of the intensity of the first reflective light which is repeatedly measured, as the representative intensity.

The processor 220 may estimate absorbance of the skin of the user based on the calculated intensity of the emitting light and the measured intensity of the second reflective light. For example, the processor 220 may estimate the absorbance of the skin of the user using Equation 1.

Figure 3:
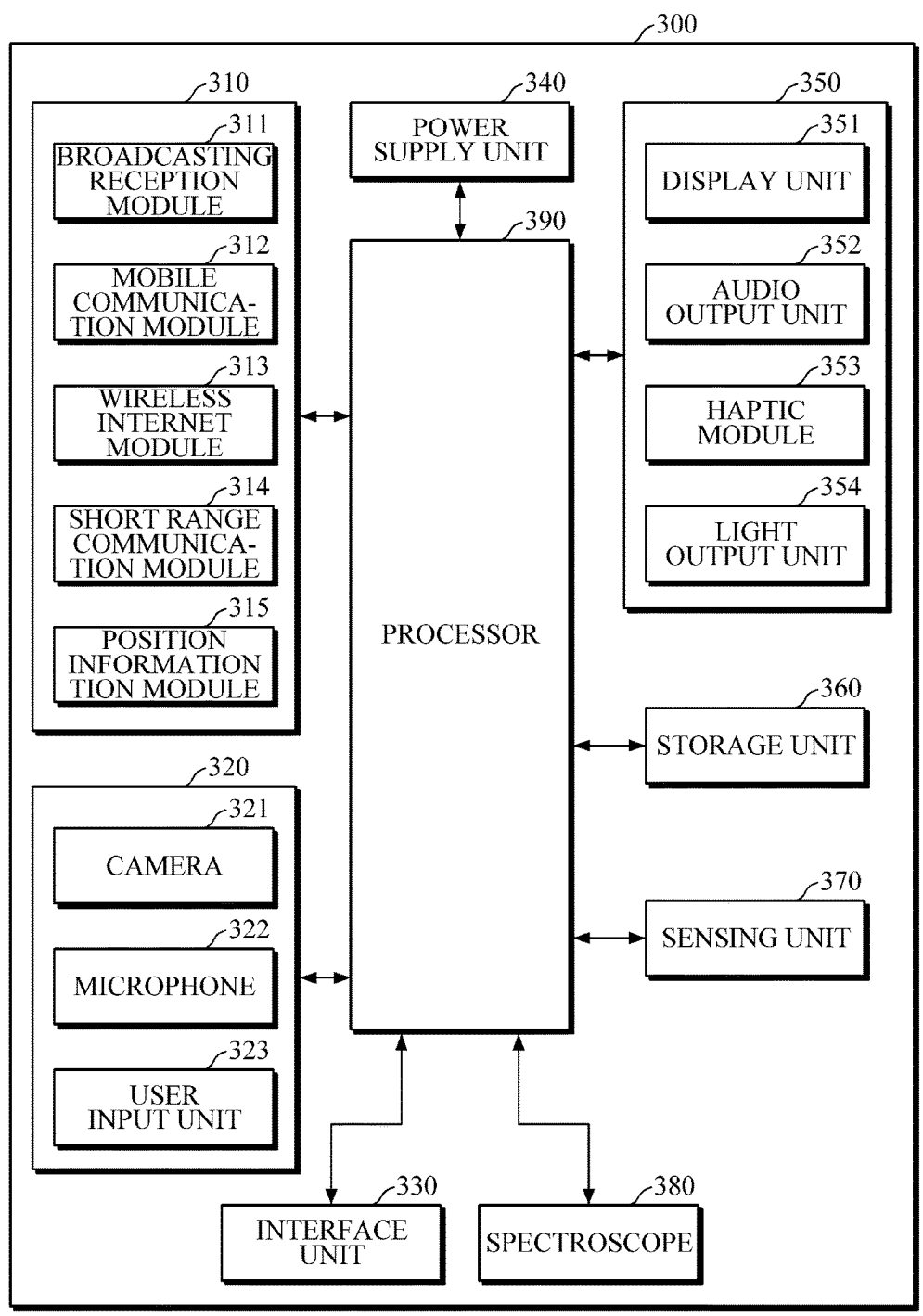
FIG. 3 is a block diagram illustrating a wearable device according to another exemplary embodiment.

FIG. 3 is a block diagram illustrating a wearable device according to another exemplary embodiment. A wearable device 300 shown in FIG. 3 may be another exemplary embodiment of the wearable device 110 shown in FIG. 1.

Referring to FIG. 3, the wearable device 300 may include a communication unit (e.g., communication interface) 310, an input unit (e.g., inputter) 320, an interface unit (e.g., interface) 330, a power supply unit (e.g., power supply) 340, an output unit 350, a storage unit (e.g., storage or memory) 360, a sensing unit (e.g., sensor) 370, a spectroscope 380, and a processor 390. Meanwhile, since all the components shown in FIG. 3 are not essential components when the wearable device 300 is implemented, the wearable device 300 may include additional components besides the components described above, and some components may be omitted.

The communication unit 310 may perform communication with an external device. In particular, the communication unit 310 may include at least one of a broadcasting reception module 311, a mobile communication module 312, a wireless Internet module 313, a short range communication module 114, and a position information module 315.

The broadcasting reception module 311 may receive a broadcasting signal and/or broadcasting related information from an external broadcasting management server through a broadcasting channel. Here, the broadcasting channel may include a satellite channel, or a terrestrial channel. Meanwhile, in an example shown in FIG. 3, the wearable device 300 including one broadcasting reception module is illustrated, but two or more broadcasting reception modules may be included for a simultaneous broadcasting reception or a broadcasting channel switching on at least two broadcasting channels.

The mobile communication module 312 may transceive a wireless signal with at least one of a base station, an external terminal, and a server on a mobile communication network constructed according to technical standards or communication methods (for example, global system for mobile communication (GSM), code division multi access (CDMA), code division multi access 2000 (CDMA 2000), enhanced voice-data optimized or enhanced voice-data only (EV-DO), wideband CDMA (WCDMA), high speed downlink packet access (HSDPA), high speed uplink packet access (HSUPA), long term evolution (LTE), long term evolution-advanced (LTE-A), etc.).

Here, the wireless signal may include various types of data according to transmission and reception of a voice call signal, a video communication call signal, or a character/multimedia message.

The wireless Internet module 313 may be a module for wireless Internet connection, and be installed internally or externally. The wireless Internet module 313 may transceive the wireless signal on a communication network according to wireless Internet technologies.

In this case, the wireless Internet technology may include wireless local area network (WLAN), wireless-fidelity (Wi-Fi), Wi-Fi direct, digital living network alliance (DLNA), wireless broadband (WiBro), world interoperability for microwave access (WiMAX), HSDPA, HSUPA, LTE, LTE-A, etc.

Meanwhile, since the wireless Internet connection by the WiBro, HSDPA, HSUPA, GSM, CDMA, WCDMA, LTE, LTE-A, etc. is performed through the mobile communication network, the wireless Internet module 313 performing the wireless Internet connection through the mobile communication network described above may be a kind of the mobile communication module 312.

The short range communication module 314 may be a module for short range communication with the external device, and support the short range communication using at least one of Bluetooth, radio frequency identification (RFID), infrared data association (IrDA), ultra wideband (UWB), ZigBee, near field communication (NFC), Wi-Fi, Wi-Fi direct, wireless universal serial bus (USB) technologies.

The position information module 315 may be a module for obtaining a position of the wearable device 300, and for example, include a global positioning system (GPS) module, or a Wi-Fi module, etc. As one example, the wearable device 300 may obtain a position of the wearable device 300 using a signal transmitted from a GPS satellite by using the GPS module. As another example, the wearable device 300 may obtain the position of the wearable device 300 based on information of a wireless access point (AP) of transmitting or receiving a wireless signal with the Wi-Fi module by using the Wi-Fi module.

The input unit 320 may input image information, audio information, or information input by the user. For this, the input unit 320 may include at least one of a camera 321, a microphone 322, and a user input unit (e.g., mouse, touchpad, keyboard, etc.) 323.

The camera 321 may process an image frame such as a still image or video, etc. obtained by an image sensor in a video telephony mode or a capture mode. The processed image frame may be displayed on a display unit (e.g., display) 351 or stored in the storage unit 360.

Meanwhile, the wearable device 300 may include a plurality of cameras 321, and the plurality of cameras 321 may be arranged in a matrix form. The wearable device 300 may receive multiple pieces of image information having various angles or focuses through the camera 321 having the matrix form. Further, the plurality of cameras 321 may be arranged to have a stereoscopic structure in order to obtain a left image and a right image for implementing a stereoscopic image.

The microphone 322 may process an external audio signal into electrical voice data. The processed voice data may be diversely used according to a function which is being performed (or an application program which is being executed) by the wearable device 300. Meanwhile, various noise rejection algorithms for removing noise generated in the process of receiving the external audio signal may be implemented in the microphone 322.

The user input unit 323 may input the information from the user. When the information is received through the user input unit 323, the processor 390 may control an operation of the wearable device 300 according to the received information. According to an exemplary embodiment, the user input unit 323 may include a mechanical input unit (e.g., a button, a dome switch, a jog wheel, a jog switch, etc. which are located in a front/back surface or a side surface of the wearable device 110), and a touch input unit. In this case, the touch input unit may be a virtual key, a soft key, or a visual key displayed on a touch screen through a software processing, or a touch key arranged in an area other than a portion in which the touch screen is arranged. Meanwhile, the virtual key or the visual key may have various forms, and be displayed on the touch screen. For example, the virtual key or the visual key may be formed by graphics, texts, icons, video, or a combination thereof.

The interface unit 330 may perform a function for interfacing with various kinds of external devices connected to the wearable device 300. According to an exemplary embodiment, the interface unit 330 may include at least one of a wired/wireless headset port, an external charger port, a wired/wireless data port, a memory card port, a port connecting a device including an identification module, an audio input/output (I/O) port, a video I/O port, an earphone port.

The power supply unit 340 may receive external power or internal power, and provide the power to each of the components included in the wearable device 300 according to control of the processor 390. For this, the power supply unit 340 may include a battery, and the battery may be an embedded battery or a replaceable battery.

The output unit 350 may generate an output related to a visible, audible, or tactile sense. For this, the output unit 350 may include at least one of the display unit 351, an audio output unit (e.g., speaker) 352, a haptic module (e.g., haptic actuator) 535, and a light output unit (e.g., light emitting diode) 354.

The display unit 351 may display information processed by the wearable device 300. For example, the display unit 351 may display execution screen information of the application program executed in the wearable device 300, or user interface (UI) or graphic user interface (GUI) information according to the execution screen information. Meanwhile, the display unit 351 may implement a touch screen by forming an interactive layer structure with a touch sensor or forming as an integral part of the touch sensor. The touch screen may perform a function of the user input unit 323 providing an input interface between the wearable device 300 and the user, and also provide an output interface between the wearable device 300 and the user.

The audio output unit 352 may output audio data which is received from the communication unit 310 or stored in the storage unit 360 in a telephony mode, a recording mode, a voice recognition mode, a broadcasting reception mode, etc. Further, the audio output unit 352 may output an audio signal related to a function (for example, call signal reception sound, message reception sound, etc.) performed by the wearable device 300. For this, the audio output unit 352 may include a receiver, a speaker, a buzzer, etc.

The haptic module 353 may generate various tactile effects (for example, a vibration, etc.) which are able to be sensed by the user. Strength and a pattern of the vibration generated by the haptic module 353 may be controlled by a selection of the user, or a setting of the processor 390. For example, the haptic module 353 may output by combining different vibrations, or sequentially output.

Further, the haptic module 353 is able to generate various tactile effects as well as the vibration. For instance, the haptic module 353 generates the effect attributed to the arrangement of pins vertically moving against a contact skin surface, the effect attributed to the injection/suction power of air though an injection/suction hole, the effect attributed to the skim over a skin surface, the effect attributed to the contact with electrode, the effect attributed to the electrostatic force, the effect attributed to the representation of hold/cold sense using an endothermic or exothermic device and the like.

Moreover, the haptic module 353 may transmit a tactile effect through a direct contact, and be implemented to allow the user to sense the tactile effect through a muscle sense of a finger, or an arm, etc. of the user. The number of haptic modules 353 may be two or more according to a configuration aspect of the wearable device 300.

The light output unit 354 may output a signal for informing of generation of an event using light of a light source of the wearable device 300. In this case, the event generated by the wearable device 300 may include message reception, call signal reception, a missed call, an alarm, a schedule alarm, e-mail reception, information reception through the application, etc.

The storage unit 360 may store a program or commands for an operation of the wearable device 300, and store data which is input/output. Further, the storage unit 360 may store data used for calculating the absorbance to the skin of the user (e.g., the intensity of the first reflective light and the intensity of the second reflective light which are measured by the spectroscope 380, the information related to the reflectivity of the reference material, the intensity of the emitting light calculated by the processor 390, etc.).

The storage unit 360 may include a flash memory type, a hard disk type, a multimedia card micro type, a card type memory (for example, a secure digital (SD) or extreme digital (XD) card, etc.), a random access memory (RAM), a static random access memory (SRAM), a read only memory (ROM), an electrically erasable programmable read only memory (EEPROM), a programmable read only memory (PROM), a magnetic memory, a magnetic disk, an optical disk, etc. Further, the wearable device 300 may manage an external storage medium such as a web storage unit performing a storage function of the storage unit 360 on the Internet.

The sensing unit 370 may sense whether the wearable device 300 is placed on the charger 120. Also, the sensing unit 370 may sense the moment at which the wearable device 300 is taken apart from the charger 120. The sensing unit 370 may include various sensors such as a pressure sensor, a proximity sensor, etc.

When the wearable device 300 is placed on the charger for charging, the spectroscope 380 may emit light to the reference material, receive the first reflective light reflected from the reference material, and measure the intensity of the first reflective light. In this case, the reference material may be a diffused reflection material having a reflectivity of 1 to 99%, and be arranged or coated on a side facing a light emitting side of the wearable device 300 when the wearable device 300 is installed for charging. The reference material may include $BaSO_4$, PTEF, etc.

According to an exemplary embodiment, when the wearable device 300 is placed on the charger, the spectroscope 380 may automatically emit the light to the reference material arranged or coated on the charger at predetermined time intervals, receive the first reflective light reflected from the reference material, and repeatedly measure the intensity of the first reflective light. In this case, the predetermined time interval may be set by the user, or as default.

Further, when the wearable device 300 is worn by the user, the spectroscope 380 may emit the light to the skin of the user according to a command of the user, receive the second reflective light reflected from the skin of the user, and measure the intensity of the second reflective light.

The processor 390 may control an overall operation of the wearable device 300. The processor 390 may execute various programs stored in the storage unit 360, and provide a variety of information to the user by processing a signal, data, information, etc. which is input or output.

The processor 390 may control at least one of the communication unit 310, the input unit 320, the interface unit 330, the power supply unit 340, the output unit 350, the storage unit 360, the charge sensing unit 370, and the spectroscope 380, in order to execute the program stored in the storage unit 360.

In more detail, when the wearable device 300 is placed on the charger for charging, the processor 390 may control the spectroscope 380 so as to emit the light to the reference material of the charger and repeatedly measure the intensity of the first reflective light. Further, when the wearable device 300 is worn by the user, the processor 390 may control the spectroscope 380 so as to emit the light to the skin of the user according to the command of the user and measure the intensity of the second reflective light.

When the wearable device 300 is removed from the charger, the processor 390 may calculate the intensity of the emitting light of the spectroscope 380 based on the intensity of the first reflective light which is repeatedly measured. For example, the processor 390 may calculate a representative intensity of the intensity of the first reflective light which is repeatedly measured, correct the calculated representative intensity according to a reflectivity of the reference material, and calculate the intensity of the emitting light. In this case, the processor 390 may calculate one of the following values, an arithmetic mean value, a weighted mean value, a median value, a mode value, a minimum value, and a maximum value, of the intensity of the first reflective light which is repeatedly measured, as the representative intensity.

The processor 390 may calculate absorbance of the skin of the user based on the calculated intensity of the emitting light and the measured intensity of the second reflective light. For example, the processor 390 may calculate the absorbance of the skin of the user using Equation 1.

With reference to FIGS. 2 and 3, the spectroscope 210 and 380 is described as including a light emitter that emits the light to the skin of the user, but the exemplary embodiments are not limited thereto. The light emitter may be disposed in the wearable device 200 and 300 separately from the spectroscope 210 and 380 so as to secure a certain distance required for the spectroscope 210 and 380 to detect a light that is emitted from the light emitter and then reflected off the skin toward the spectroscope 210 and 380.

Figure 4A:
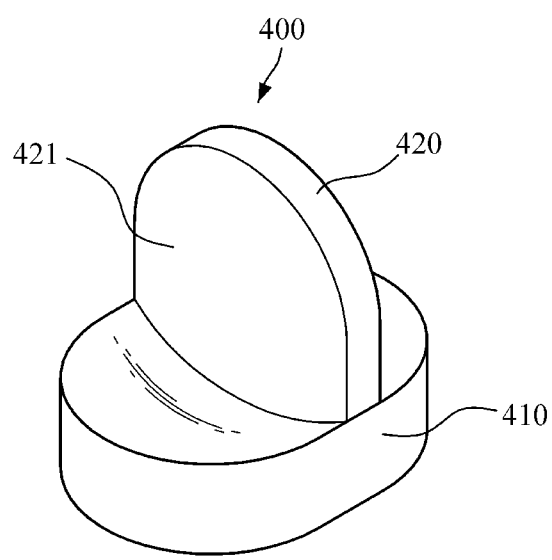
FIG. 4A is a block diagram illustrating a charger according to an exemplary embodiment.
Figure 4B:
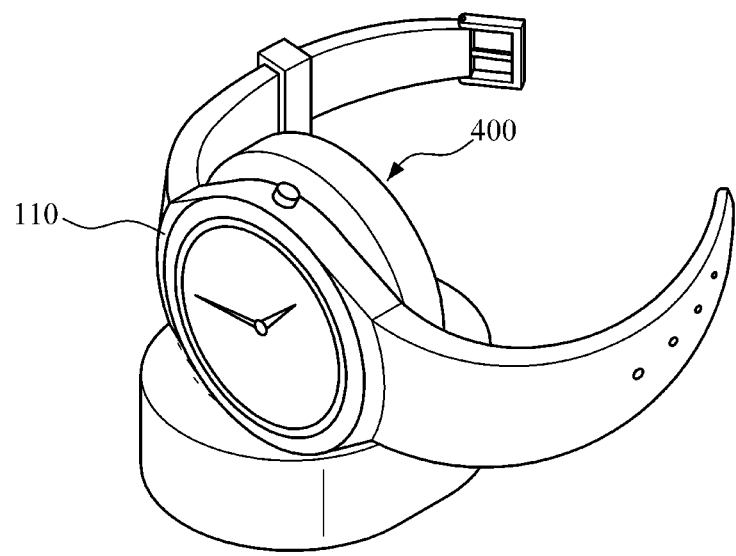
FIG. 4B is a diagram illustrating a state in which a wearable device is placed on the charger shown in FIG. 4A.

FIG. 4A is a block diagram illustrating a charger according to an exemplary embodiment, and FIG. 4B is a diagram illustrating a state in which a wearable device is placed on the charger shown in FIG. 4A. FIGS. 4A and 4B illustrate a charger of a wristwatch type or wristband type wearable device.

Referring to FIGS. 4A and 4B, a charger 400 may include a lower body 410 on which the wearable device 110 is placed, and a support body 420 supporting so that the wearable device 110 is not inclined. FIG. 4A illustrates a structure in which the lower body 410 is separated from the support body 420, but the lower body 410 may be implemented integrally with the support body 420.

The lower body 410 may be implemented in a structure in which the wearable device 110 is naturally located in a chargeable region when the wearable device is placed according to a shape of the wearable device 110. For example, the lower body 410 may have a cylindrical shape, and be implemented to have a structure in which its edge portion is higher than its center portion. However, the structure of the lower body 410 is merely an embodiment, and be diversely implemented.

When the wearable device 110 is placed on the lower body 410, the support body 420 may be formed at a right angle with the lower body 410 in order to support the wearable device 110 so as not to be inclined.

When the wearable device 110 is installed, the support body 420 may have a side facing the wearable device 110, that is, a side 421 facing the light emitting side of the wearable device 110, and the reference material may be arranged or coated on the side 421. In this case, the reference material may be a diffused reflection material having a reflectivity of 1 to 99%, and include $BaSO_4$, PTEF, etc.

Figure 5A:
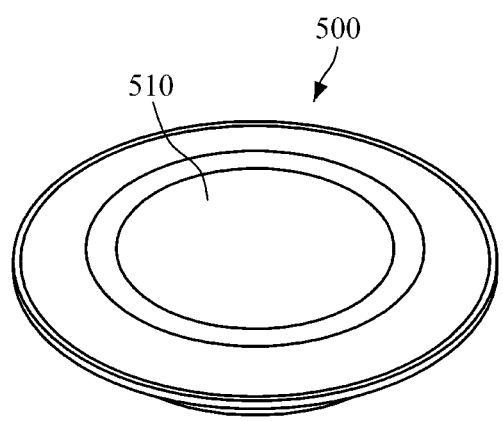
FIG. 5A is a diagram illustrating a charger according to another exemplary embodiment.
Figure 5B:
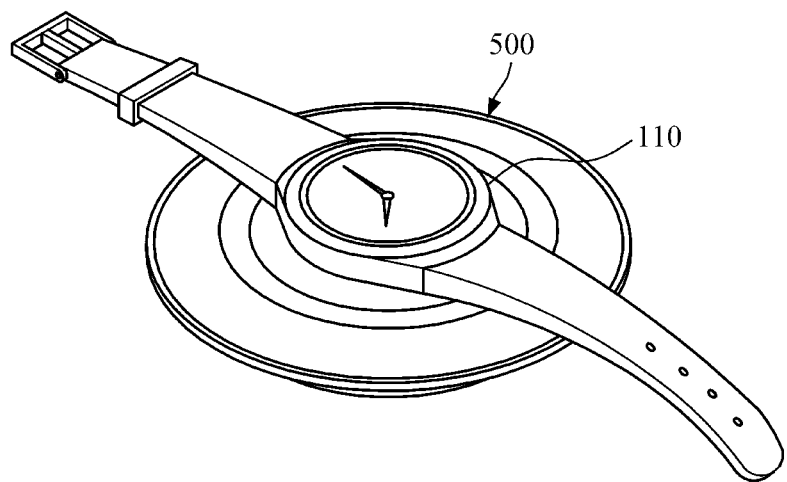
FIG. 5B is a diagram illustrating a state in which a wearable device is placed on the charger shown in FIG. 5A.

FIG. 5A is a diagram illustrating a charger according to another exemplary embodiment, and FIG. 5B is a diagram illustrating a state in which a wearable device is placed on the charger shown in FIG. 5A. FIGS. 5A and 5B illustrate a charger of a wristwatch type or wristband type wearable device.

Referring to FIGS. 5A and 5B, a body of a charger 500 may be implemented to have a round shape, and when the wearable device 110 is installed, have a side facing the wearable device 110, that is, an upper side 510 facing the light emitting side of the wearable device 110, and the reference material may be arranged and coated on the upper side 510. In this case, the reference material may be a diffused reflection material having a reflectivity of 1 to 99%, and include $BaSO_4$, PTEF, etc.

Meanwhile, FIGS. 5A and 5B illustrate an example in which the body of the charger 500 is circular in shape, and the upper side is implemented as a plane, but according to an exemplary embodiment, the body of the charger 500 may be implemented in various shapes such as square, pentagon, triangle, hexagon, etc. The body of the charger 500 may be implemented to have a structure in which the wearable device 110 is able to be naturally located in a chargeable region of the upper side when the wearable device 110 is placed on the upper side.

Figure 6:
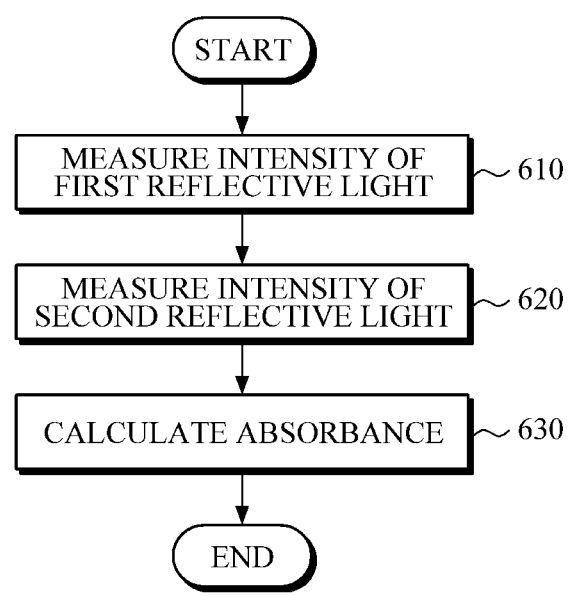
FIG. 6 is a flowchart for describing a method for estimating absorbance of a wearable device according to an exemplary embodiment.

FIG. 6 is a flowchart for describing an embodiment of a method for estimating absorbance of a wearable device. In this case, as described above, the wearable device may be a device which is worn by the user and is able to estimate the absorbance of the skin of the user, and include the wearable device having various types such as a wristwatch type, a wristband type, a ring type, a belt type, a necklace type, an ankle band type, a thigh band type, a forearm band type, etc.

Referring to FIGS. 1 and 6, when the wearable device 110 is placed on the charger 120 for charging, the wearable device 110 may emit the light to the reference material arranged or coated on the charger 120, receive the first reflective light reflected from the reference material, and measure the intensity of the first reflective light (operation S610).

When the wearable device 110 is removed from the charger 120 and is worn by the user, the wearable device 110 may emit the light to the skin of the user, receive the second reflective light reflected from the skin of the user, and measure the second reflective light (operation S620).

The wearable device 110 may calculate the absorbance of the skin of the user based on the first reflective light and the second reflective light (operation S630).

According to another exemplary embodiment, the operation 610 may be omitted, and instead a predetermined intensity value may be stored in the wearable device 110 as the first reflective light.

Hereinafter, a method for estimating absorbance of the wearable device will be described in detail with reference to FIG. 7.

Figure 7:
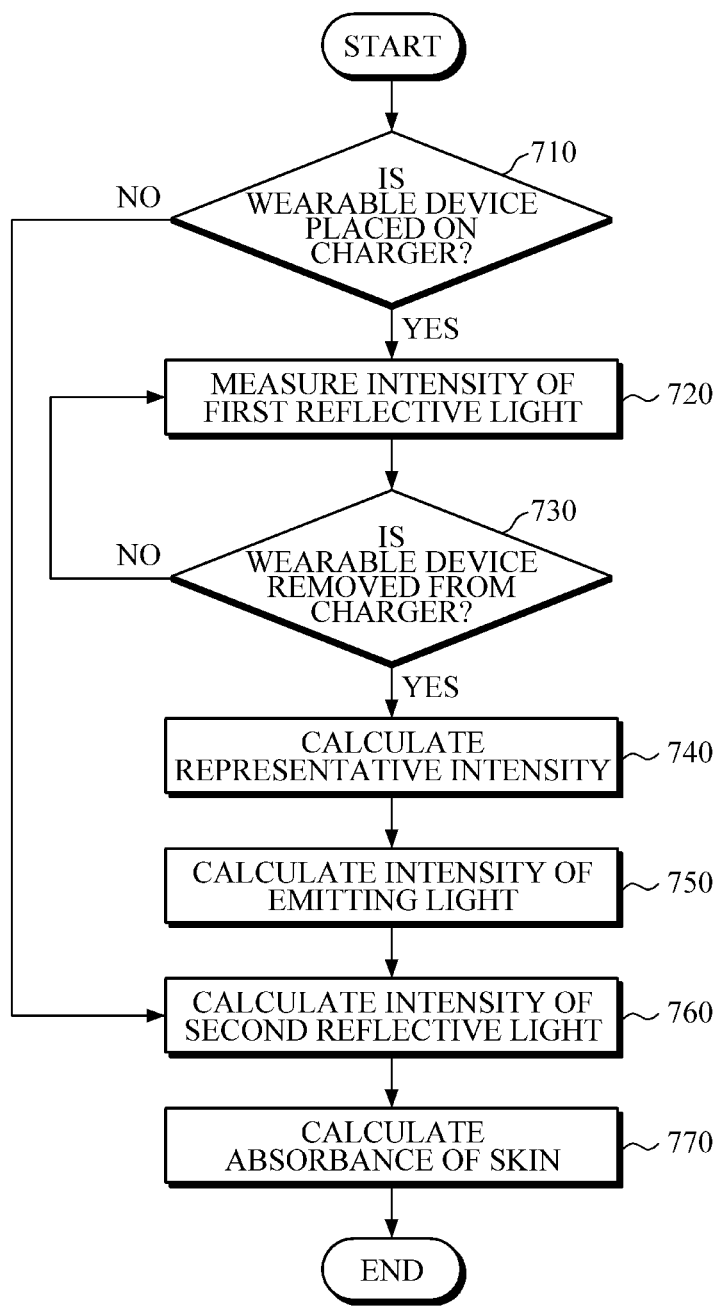
FIG. 7 is a detailed flowchart for describing a method for estimating absorbance of a wearable device according to an exemplary embodiment.

FIG. 7 is a detailed flowchart for describing a method for estimating absorbance of a wearable device.

Referring to FIGS. 1 and 7, the wearable device 110 may determine whether the wearable device 110 is placed on the charger 120 (operation S710).

When the wearable device 110 is placed on the charger 120, the wearable device 110 may automatically emit the light to the reference material arranged or coated on the charger 120, receive the first reflective light reflected from the reference material, and measure the intensity of the first reflective light (operation S710). In this case, the reference material may be a diffused reflection material having a reflectivity of 1 to 99%, and be arranged or coated on a side facing the light emitting side of the wearable device 110 when the wearable device 110 is installed for charging. In this case, the reference material may include $BaSO_4$, PTEF, etc.

The wearable device 110 may determine whether the wearable device 110 is removed from the charger 120 (operation S730), and when the wearable device 110 is not removed, emit the light to the reference material of the charger 120 by proceeding to the operation 720, receive the first reflective light reflected from the reference material, and repeatedly measure the intensity of the first reflective light (operation S720). In this case, the repeated measurement of the intensity of the first reflective light may be performed at predetermined time intervals.

When the wearable device 110 is removed from the charger 120, the wearable device 110 may calculate a representative intensity representing the intensity of the first reflective light which is repeatedly measured (operation S740). For example, the wearable device 110 may calculate one of the following values, an arithmetic mean value, a weighted mean value, a median value, a mode value, a minimum value, and a maximum value of the intensity of the first reflective light which is repeatedly measured, as the representative intensity.

The wearable device 110 may calculate the intensity of the emitting light emitted from the wearable device 110 based on the calculated representative intensity (operation S750). For example, the wearable device 110 may calculate the intensity of the emitting light by correcting the calculated representative intensity according to the reflectivity of the reference material.

When the wearable device 110 is worn by the user, the wearable device 110 may emit the light to the skin of the user, receive the second reflective light reflected from the skin of the user, and measure the intensity of the second reflective light (operation S760). In this case, the measurement of the intensity of the second reflective light may be performed according to an input of the user.

The wearable device 110 may calculate the absorbance of the skin of the user based on the intensity of the emitting light and the intensity of the second reflective light (operation S770). For example, the wearable device 110 may calculate the absorbance of the skin of the user using Equation 1.

While not restricted thereto, an exemplary embodiment can be implemented as computer readable codes in a computer readable recording medium. Codes and code segments constituting the computer program can be easily inferred by a skilled computer programmer in the art. The computer readable recording medium includes all types of recording media in which computer readable data can be stored. Examples of the computer readable recording medium include a ROM, a RAM, a compact disc (CD)-ROM, a magnetic tape, a floppy disk, and an optical disk, etc. Further, the computer readable recording medium may be distributed to computer systems over a network in which computer readable codes may be stored and executed in a distributed manner. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A wearable device comprising:
    a spectroscope configured to emit a first light to a reference material of a charger in response to the wearable device being placed on the charger, measure an intensity of the first light reflected from the reference material, emit a second light to a skin of a user while the wearable device is worn by the user, and measure an intensity of the second light reflected from the skin of the user; and
    a processor configured to determine absorbance of the skin of the user based on the intensity of the first light that is measured while the wearable device is placed on the charger and the intensity of the second light that is measured while the wearable device is worn by the user.

2. The wearable device of claim 1, wherein, when the wearable device is worn by the user, the spectroscope is configured to emit the second light to the skin of the user and measure the intensity of the second light according to an input of the user.

3. The wearable device of claim 1, the reference material comprises at least one of barium sulfate (BaSO4) and polytetrafluoroethylene.

4. The wearable device of claim 1, further comprising a sensor configured to sense whether the wearable device is placed on the charger.

5. The wearable device of claim 1, wherein the wearable device is a wristwatch type or wristband type wearable device.

6. A wearable device comprising:
    a spectroscope configured to emit first light to a reference material of a charger at predetermined time intervals, repeatedly measure an intensity of the first light reflected from the reference material, emit second light to a skin of a user, and measure an intensity of the second light reflected from the skin of the user; and
    a processor configured to determine absorbance of the skin of the user based on the intensity of the first light and the intensity of the second light,
    wherein the processor is further configured to determine a representative intensity representing the intensity of the first light which is repeatedly measured in response to the wearable device being removed from the charger.

7. The wearable device of claim 6, wherein the processor is further configured to determine at least one of an arithmetic mean value, a weighted mean value, a median value, a mode value, a minimum value, and a maximum value of the intensity of the first light which is repeatedly measured, as the representative intensity.

8. The wearable device of claim 6, wherein the processor is further configured to determine an intensity of emitting light of the spectroscope by correcting the representative intensity according to a reflectivity of the reference material, and determine the absorbance of the skin of the user using the determined intensity of the emitting light and the intensity of the second light.

9. A method for operating a wearable device, the method comprising:
    emitting a first light to a reference material of a charger in response to the wearable device is placed on the charger;
    measuring an intensity of the first light reflected from the reference material;
    emitting a second light to a skin of a user while the wearable device is worn by the user;
    measuring an intensity of the second reflected from the skin of the user; and
    determining absorbance of the skin of the user based on the intensity of the first light that is measured while the wearable device is placed on the charger and the intensity of the second light that is measured while the wearable device is worn by the user.

10. The method according to claim 9, wherein the reference material comprises at least one of barium sulfate (BaSO4) and polytetrafluoroethylene (PTEF).

11. The method according to claim 9, wherein the wearable device is a wristwatch type or wristband type wearable device.

12. A method for operating a wearable device, the method comprising:
    emitting first light to a reference material of a charger at predetermined time intervals;
    repeatedly measuring an intensity of the first light reflected from the reference material;
    emitting second light to a skin of a user;
    measuring an intensity of the second light reflected from the skin of the user;
    determining absorbance of the skin of the user based on the intensity of the first light and the intensity of the second light;
    determining a representative intensity representing the intensity of the first light which is repeatedly measured in response to the wearable device being removed from the charger; and
    correcting the representative intensity based on a reflectivity of the reference material,
    wherein the determining the absorbance of the skin of the user comprises determining the absorbance based on the corrected representative intensity and the intensity of the second light.

13. The method according to claim 12, wherein the determining the representative intensity comprises determining at least one of an arithmetic mean value, a weighted mean value, a median value, a mode value, a minimum value, and a maximum value of the intensity of the first light which is repeatedly measured, as the representative intensity.

14. A wearable device comprising:
    a light emitter configured to emit a first light to a charger in response to the wearable device being placed on the charger, and emit a second light to a user of the wearable device while the wearable device is detached from the charger and worn by the user;
    a spectroscope configured to receive the first light reflected from the charger and measure a reference reflective intensity of the first light, and receive the second light reflected from the user and measure an intensity of the second light;

a storage configured to store the reference intensity of the first light; and a processor configured to determine absorbance of the user based on a comparison between the reference reflective intensity of the first light stored in the storage and the intensity of the second light measured by the spectroscope.

\* \* \* \* \*